US009789229B1

(12) United States Patent
Lareau et al.

(10) Patent No.: US 9,789,229 B1
(45) Date of Patent: *Oct. 17, 2017

(54) CATHETER SHAFT WITH ENHANCED PLATELET ANTI-ADHESION SURFACES

(71) Applicants: Raymond Lareau, Westford, MA (US); Benjamin Bell, Shrewsbury, MA (US); Jeannette Ho, Toronto (CA); J. Paul Santerre, Whitby (CA)

(72) Inventors: Raymond Lareau, Westford, MA (US); Benjamin Bell, Shrewsbury, MA (US); Jeannette Ho, Toronto (CA); J. Paul Santerre, Whitby (CA)

(73) Assignee: Angio Dynamics Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,145

(22) Filed: Mar. 17, 2014

Related U.S. Application Data

(60) Provisional application No. 61/791,863, filed on Mar. 15, 2013.

(51) Int. Cl.
| | |
|---|---|
| *A61L 29/04* | (2006.01) |
| *C08G 18/10* | (2006.01) |
| *C08G 18/48* | (2006.01) |
| *C08L 75/04* | (2006.01) |
| *C08G 18/73* | (2006.01) |
| *A61L 29/12* | (2006.01) |
| *A61L 29/18* | (2006.01) |
| *A61L 29/14* | (2006.01) |
| *A61M 25/00* | (2006.01) |
| *A61L 33/06* | (2006.01) |

(52) U.S. Cl.
CPC .......... *A61L 29/126* (2013.01); *A61L 29/049* (2013.01); *A61L 29/14* (2013.01); *A61L 29/18* (2013.01); *A61L 33/062* (2013.01); *A61M 25/0017* (2013.01); *C08L 75/04* (2013.01); *A61L 2300/802* (2013.01)

(58) Field of Classification Search
CPC ........ A61L 29/14; A61L 29/18; A61L 29/041; A61L 29/049; A61L 33/062; A61L 33/064; A61L 2300/802; A61M 25/0017; A61M 25/0021; A61M 2025/0056; C08L 75/04; C08L 75/06; C08L 75/08

USPC .................. 524/423; 504/523, 529
See application file for complete search history.

(56) References Cited

U.S. PATENT DOCUMENTS

| | | | | | |
|---|---|---|---|---|---|
| 5,498,377 | A | * | 3/1996 | Ozaki ................ | A61M 25/001 156/244.13 |
| 5,879,499 | A | * | 3/1999 | Corvi ................ | A61M 25/0012 156/173 |
| 6,127,507 | A | * | 10/2000 | Santerre ............. | A61L 33/0076 428/423.1 |
| 6,890,321 | B2 | * | 5/2005 | Luther .............. | A61M 25/0606 604/164.01 |
| 2008/0154186 | A1 | * | 6/2008 | Appling ............. | A61M 25/003 604/43 |
| 2008/0228253 | A1 | * | 9/2008 | Mullick ................ | C08G 18/10 623/1.1 |
| 2010/0249824 | A1 | * | 9/2010 | Kishida ............. | A61M 25/0122 606/194 |

OTHER PUBLICATIONS

Jahangir et al., "Fluorinated surface-modifying macromolecules: modulating adhesive protein and platelet interactions on a polyether-urethane", Journal of Biomedical Materials Research Part A, 60, 135-137, Apr. 2002.*
Szycher, "Blood Compatible Materials and Devices" pp. 45-49, Jan. 18, 1990.*

* cited by examiner

*Primary Examiner* — Christopher M Rodd

(57) ABSTRACT

A venous access catheter shaft and method of using and manufacturing such a catheter is provided. In one aspect of the invention, a catheter is provided comprising a base polymer having a Shore A durometer of 85A or lower, with 2.0% percent by weight of surface modifier, and a radiopaque filler comprising between 20-40 percentage by weight. In another aspect of the invention, a method reducing thrombus accumulation on a venous access catheter is provided wherein the catheter surface's resistance to thrombus formation is enhanced during indwell time by lowering the durometer rating of the base polymer of the catheter without increasing the amount of surface modifier additive. In another aspect of the invention, a method of manufacturing a catheter shaft is provided, wherein the shaft is formed comprising a base polymer having a Shore A durometer of 85A or lower, with 2.0% percent by weight of surface modifier, and a radiopaque filler comprising 30% by weight barium sulfate, and optionally a colorant of 0.2% weight.

12 Claims, 1 Drawing Sheet

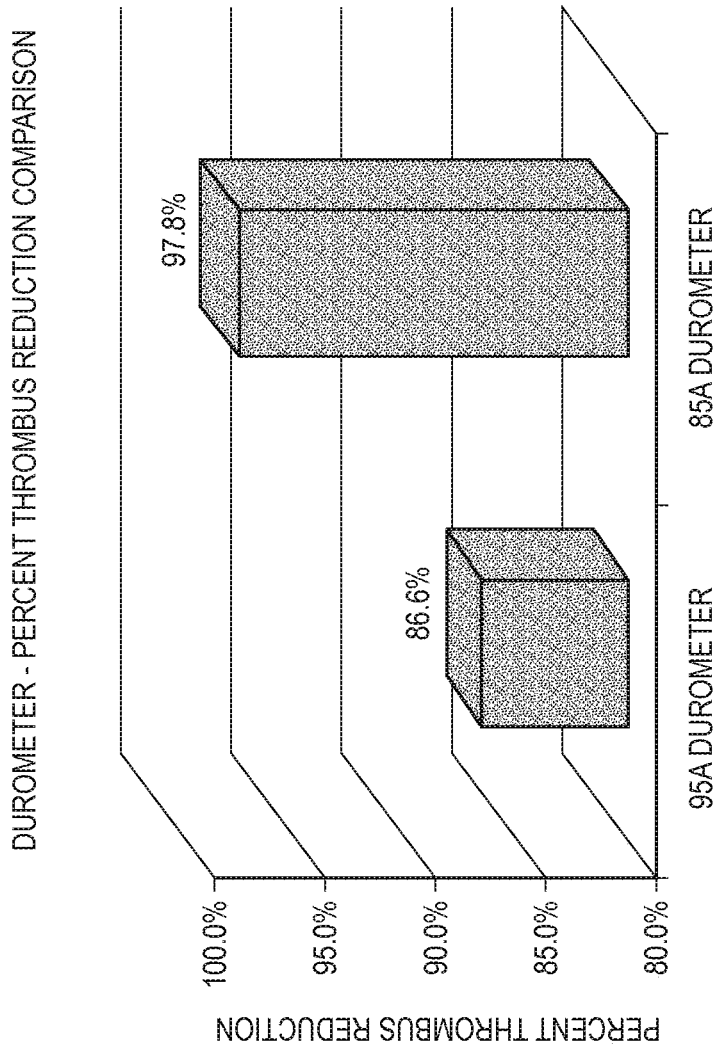

CATHETER SHAFT WITH ENHANCED PLATELET ANTI-ADHESION SURFACES

CROSS-REFERENCE TO RELATED APPLICATIONS

This application claims priority to U.S. Provisional Patent Application Ser. No. 61/791,863 filed Mar. 15, 2013, entitled "Catheter Shaft with Enhanced Platelet Anti-Adhesion Surfaces."

FIELD OF THE INVENTION

The present invention relates to a medical device apparatus and method for using and manufacture of such. More particularly, the present invention relates to indwelling venous access catheter devices comprising a shaft having a fluoropolymer additive and a polymer base within a specific durometer range.

BACKGROUND OF THE INVENTION

Venous access catheters provide venous access to the central circulatory system. Venous access catheters include central venous catheters, midlines dialysis catheters, implantable ports and peripherally inserted central catheters, also known as PICC lines. The access line or port with attached catheter is used for the delivery of intravenous fluids, medications such as chemotherapy drugs and antibiotics, and blood products. Venous access catheters may also be used as access mechanisms for blood sampling and the administration of contrast agents during diagnostic Computer Tomography (CT) procedures.

One type of venous access catheters, a PICC line, provides venous access to the central circulatory system through a peripheral vein. Central venous catheters or CVCs also provide access to the venous system but are inserted through a larger vein, closer to the heart. Yet another type of venous access catheter, the dialysis catheter, provides either acute or chronic venous access to the central circulatory system for filtering of blood during a dialysis procedure. Implantable ports provide subcutaneous access to the venous system via needle inserted septum defining a reservoir in fluid communication with a catheter shaft. PICCs, CVC, ports and dialysis catheter shafts come in a variety of configurations. These include single lumen, dual lumen and other multi-lumen configurations. They come in various lengths to accommodate different anatomy and catheter insertion sites.

Venous access devices are designed to remain within the patient for a period of days to a year or even longer, and can be accessed in an inpatient, outpatient or home setting. One of the most common complications resulting from long term implantation of venous access devices is the buildup of thrombus on the indwelling portion of the catheter due to blood platelet adhesion on the catheter shaft surfaces. In addition, a fibrin sheath, or fibrin layer, may form along the vein entry site or may grow over the catheter tip forming what is known as fibrin tail.

Thrombus can appear anywhere on a catheter surface which is exposed to the bloodstream, but clot formation is often most extensive at the distal section of the catheter near the tip and that portion of the shaft proximate to the venotomy insertion site. Localized thrombus buildup on the catheter can result in various complications which compromise the performance of the indwelling device including increased catheter related blood stream infection, complete or partial catheter occlusion and non-laminar blood flow. Both adherent fibrin and platelet adhesion can interact to further promote thrombus build-up. Complications from fibrin and clot buildup may necessitate additional procedures to mechanically disrupt the clot mass or the administration of anti-thrombotic medications such as TPA or other thrombolytic drug. In some cases, the catheter must be removed and replaced.

The prevention of thrombus formation on catheter shaft surfaces has been the subject of much research and product development efforts in the medical device community. For example, attempts to prevent or minimize thrombus formation on catheter surfaces have focused on catheter coatings including anticoagulants, such as heparin The main disadvantage of coatings is the tendency of the coating to elude from the shaft after implantation resulting in reduced long-term protection against thrombus formation.

U.S. Pat. No. 6,127,507, which is incorporated herein by reference for all purposes, describes the use of certain fluoroalkyl surface-modifying macromolecules in admixture with elastomers for the manufacture of blood-contacting medical devices. Such macromolecules have shown to be clinically effective in the reduction in thrombosis formation. The admixtures, also known as surface modifying additives, when used are preferably synthesized in a manner that they contain a base polymer compatible segment and terminal hydrophobic fluorine components which are non-compatible with the base polymer. The compatible segment of the surface modifier is selected to provide an anchor for the surface modifier within the base polymer substrate upon admixture. While not being bound by theory, it is believed that the fluorine tails are responsible in part for carrying the surface modifier to the surface of the admixture, with the chemical resistant fluorine chains exposed out from the surface. The latter process is believed to be driven by the thermodynamic incompatibility of the fluorine tail with the polymer base substrate, as well as the tendency towards establishing a low surface energy at the mixture's surface. When the balance between anchoring and surface migration is achieved, the surface modifier remains stable at the surface of the polymer, while simultaneously altering surface properties.

Embodiments of SMM fluoropolymer additives used in the present invention may be synthesized using a multi-functional isocyanate, a multi-functional soft segment precursor reactive therewith, and a mono function polyfluoroalcohol. The isocyanate is preferably, but not so limited to be di-functional in nature, in order to favour the formation of a linear SMM. Linear as opposed to branched or crosslinked SMM have better migration properties within the polyurethane substrate. A preferred diisocyanate for biomedical applications is 1,6-hexanediisocyanate. The soft segment precursor molecule is preferably di-functional in nature but not so limited to be di-functional, in order to favour the formation of a linear SMM. Again, linearity favours migration properties within the base polymer substrate. Examples of typical soft segment precursors include, polypropylene oxide polyols of molecular weight 1000, and polytetramethylene oxide diols of molecular weight 1000. SMM's are synthesized using a preliminary prepolymer method similar to the classical one used for polyurethanes. However, the subsequent step differs in that a chain extension is not carried out. A mono-functional oligomeric fluorinated alcohol is used to cap the prepolymer, rather than chain extend the prepolymer. The fluorinated alcohol preferably has a single fluoro-tail but is not limited to this feature. A general formula for the oligomeric fluoro-alcohol of use in the invention is H—$(OCH_2CH_2)_n$—$(CF_2)_m$—$CF_3$, wherein n can range from 1 to 10, but preferably ranges from 1 to 4, and m can range from 1 to 20 but preferably ranges from 2 to 12. A general guide for the selection of "n" relative to "m" is that "m" should be equal or greater to "2n" in order to minimize the likelihood of the $(OCH_2CH_2)_n$ segment displacing the $(CF_2)_m$—$CF_3$ from the surface following exposure to water, since the former is more hydrophilic than the fluorotail and will compete with the fluorotail for the surface. Without being bound by theory, the presence of the $(OCH_2CH_2)_n$ segment is believed to be important to the function of the SMM because it provides a highly mobile spacer segment between the fluorotail and the substrate. This is important in order to effectively expose the fluorosurface to, for example, an aqueous medium. Examples of typical oligomeric fluoroalcohols include various fractions BA-L, BA-N, FSO-100 and FSN-100 (DuPont de Nemours, Wilmington, Del.).

In some embodiments, the catheter comprises a polymeric material comprising a fluoropolymer comprising terminal polyfluoro-oligomeric groups, wherein the fluoropolymer is characterized by a polystyrene equivalent weight average molecular weight ($M_w$) greater than 13,000 Daltons (13 kDa). In particular embodiments, the fluoropolymer can contain less than 10% (w/w) (e.g., from 0% to 1.5%, 0% to 2%, 0.1% to 2.2%, 0.3% to 3%, 0% and 5%, or 0.5% to 5% (w/w)) trimer formed by reaction of one diisocyanate with two perfluorinated alcohols to form a low molecular weight fluoropolymer component containing no soft segment. In certain embodiments, the fluoropolymer can have a polystyrene equivalent weight average molar mass, $M_w$, of from 2,000 to 26,000 g/mole (e.g., 6,000±4,000, 8,000±4,000, 10,000±4,000, 12,000±4,000, 18,000±4,000, 20,000±4,000, 22,000±4,000, or 24,000±2,000 g/mole). In some embodiments, the fluoropolymer can have a polystyrene equivalent number average molar mass, $M_n$, of from 2,000 to 18,000 g/mole (e.g., 6,000±4,000, 8,000±4,000, 10,000±4,000, 13,000±2,000, 14,000±2,000, 15,000±2,000, or 16,000±2,000 g/mole). The fluoropolymer can have a polydispersity index of between 1.0 and 2.0 (e.g., a polydispersity of 1.1 to 1.4, 1.3 to 1.6, 1.35 to 1.55, 1.5 to 1.7, or 1.6 to 1.9). For example, the fluoropolymer can have a polystyrene equivalent weight average molar mass, $M_w$, of from 2,000 to 14,000 g/mole (e.g., 6,000±4,000, 8,000±4,000, or 12,000±2,000 g/mole), and/or a polystyrene equivalent number average molar mass, $M_n$, of from 2,000 to 12,000 g/mole (e.g., 6,000±4,000, 8,000±4,000, or 10,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Alternatively, the fluoropolymer can have a polystyrene equivalent weight average molar mass, $M_w$, of from 14,000 to 26,000 g/mole (e.g., 18,000±4,000, 20,000±4,000, or 22,000±4,000 g/mole), and/or a polystyrene equivalent number average molar mass, $M_n$, of from 10,000 to 16,000 g/mole (e.g., 12,000±2,000 or 14,000±2,000 g/mole), and comprises between 0% and 3% (w/w) (e.g., from 0% to 1.5%, 0% to 2%, 0.1% to 2%, 0.1% to 2.2%, 0.3% to 2.2%, or 0.5% to 2.5% (w/w)) trimer. Fluoropolymer of desired size distribution and composition can be prepared, for example, by reducing the amount of diisocyanate used to make the fluoropolymer and/or by fractionating (i.e., by column chromatograph, dialysis, or extraction) the fluoropolymer.

Unlike coating technologies which are prone to degradation over time due to elution, the admixture described in the '507 patent may be added to a base polymer to create a compound in which the admixture is uniformly dispersed throughout. When the compound is extruded to form a catheter tube, the admixture becomes integral to the catheter shaft i.e., evenly dispersed throughout the wall of the shaft including inner and outer wall surfaces and any cut surface. As such, the catheter is not subject to surface elution or coating wear, but instead is capable of maintaining thrombo-resistance levels throughout indwelling time of the device.

Early test results of venous access devices formed with the surface modifier admixture described in the '507 patent, confirmed a significant reduction in platelet and thrombus adhesion when compared to devices having no anti-thrombotic features. In a standard blood loop study using an AngioDynamics PICC catheter manufactured with the surface modifier admixture (trademark ENDEXO), there was an 87% reduction in platelet and thrombus adhesion when compared to a PICC catheter containing no anti-thrombotic additives or coatings, the ENDEXO PICC catheter showed only minimal thrombus. The control PICC catheter, on the other hand, showed extensive thrombus accumulation. It is believed that the fluorine macromolecules present in the admixture help to create a catheter surface to which blood platelets and fibrin growth do not easily attach.

In an effort to further optimize the thrombus reduction qualities of a catheter shaft formed from the polymer with the surface modifier admixture described above, the inventors believe that lowering the durometer of the base polymer material will further enhance the overall thrombo-resistance of the device. Durometer is a measurement of the hardness of the base polymer material. The Shore A scale is commonly used in softer polymer measurements, with a higher number indicating a harder material. A softer (lower) durometer base polymer exhibits a higher level of micro-hydration than a harder (higher) durometer material when exposed to body temperatures and fluids. In addition, the softer material will have a greater tendency to develop surface micro-pores or "micro-cracks" under in vivo conditions which enhance surface area presentation of the surface modifier. These pathways may enhance the presentation of the fluorine macromolecules toward the catheter shaft surfaces, further improving the overall effectiveness of catheter against thrombus. Thus, due to the preferential presentation of the fluorine macromolecules through the softer durometer polymer material of the shaft, the previously demonstrated thrombus reduction rates of up to 87% may be further improved.

SUMMARY OF THE INVENTION

According to the principles of the present invention, a venous access catheter shaft and method of using and manufacturing such a catheter is provided. In one aspect of the invention, a catheter is provided comprising a base polymer having a Shore A durometer of 85A or lower, with 2.0% percent by weight of surface modifier, and a radiopaque filler comprising between 20-40 percentage by weight. In another aspect of the invention, a method reducing thrombus accumulation on a venous access catheter is provided wherein the catheter surface's resistance to thrombus formation is enhanced during indwell time by lowering the durometer rating of the base polymer of the catheter without increasing the amount of surface modifier additive. In another aspect of the invention, a method of manufacturing a catheter shaft is provided, wherein the shaft is formed comprising a base polymer having a Shore A durometer of 85A or lower, with 2.0% percent by weight of surface modifier, and a radiopaque filler comprising 30% by weight barium sulfate, and optionally a colorant of 0.2% weight.

BRIEF DESCRIPTION OF THE DRAWINGS

The above and further advantages of the invention may be better understood by referring to the following description in conjunction with the accompanying drawings, in which:

FIG. 1 depicts the percent thrombus reduction achieved using an 85 Shore durometer Carbothane resin as compared to a 95A Shore durometer Carbothane resin.

EXPERIMENTAL RESULTS

In the experimental examples described below, the measured thrombus accumulation after accelerated blood exposure time was found to be significantly lower on catheter shafts formed using a lower Shore A durometer polymer, with all other extrusion and material parameters being equal. The catheter shaft samples formed with a lower durometer polymer exhibited enhanced thrombo-resistance with a reduction in platelets and thrombus adherence by 98%, rather than the 87% observed with higher durometer relative to untreated control catheters.

Two separate thrombo-resistance studies were conducted, each comparing the thrombus accumulation under accelerated emulated indwell conditions using catheter shafts formed with the ENDEXO additive against comparable competitive catheters without any coating or additives (unloaded shafts). The first study was conducted using catheter shafts comprising 95A durometer Carbothane polymer ENDEXO compound. The second study used catheter shafts comprising an 85A durometer Carbothane polymer ENDEXO compound and compared thrombo-resistance levels between the ENDEXO loaded shafts and unloaded competitive catheter shafts. The ENDEXO catheter data from both studies were then compared. As described below, the test results confirmed that the 85A shore durometer ENDEXO catheters exhibited a 98% improvement in thrombo-resistance relative to the unloaded competitive shafts while the 95A shore durometer ENDEXO catheters exhibited an 86% improvement in thrombo-resistance relative to unloaded shaft.

Experiment 1

The shafts were tested using a well-accepted in-vitro blood loop experiment commonly used by the medical device industry to evaluate thrombogenicity of devices and materials. Catheter shafts containing ENDEXO formed using a 95A shore durometer Carbothane resin were compared against competitive unloaded PICC shafts. All catheters were 5 French, dual-lumen configurations rated for CT power injection.

The in-vitro study consisted of fresh bovine blood anticoagulated with heparin and circulated through a tubing conduit into which the test samples were inserted. The blood was maintained at a temperature of 37° C. and circulated through the conduit at a flow rate of 200 ml a minute for up to 120 minutes. To quantify thrombus adhesion on the catheters, the autologous platelets were radiolabeled with $^{111}$indium Oxine and then added back into the blood fluid before starting the experiment. After exposure, the catheter shafts were removed from the conduit, gently rinsed in saline, sectioned, and then placed in counting vials for radiation measurement in a gamma counter. Thrombus adhesion levels were quantified based on the exhibited radiation levels for the test sets. The average percent reduction in thrombus formation on the ENDEXO loaded PICC catheter shafts was determined relative to the competitive unloaded catheter shafts.

In summary, the 95A durometer ENDEXO catheter shaft samples showed an average of 86.6% percent reduction in thrombus accumulation on the shaft surface when compared with unloaded competitive test samples.

Experiment 2

ENDEXO catheter shafts formed using a 85A shore durometer Carbothane resin were compared against competitive unloaded port shafts. All catheters were 6 French, single lumen configurations rated for CT power injection. The shafts were tested for thrombogenicity using the in-vitro blood loop experiment described in Experiment 1 (FIG. 1) with the goal of demonstrating that the ENDEXO port catheter shafts showed a significant reduction in thrombus formation as compared with competitive catheter shafts of the same configuration.

The percent reduction in thrombus formation on the ENDEXO loaded catheter shafts relative to the competitive unloaded catheter shafts averaged 97.9%.

In summary, the 85A durometer ENDEXO catheter shaft samples showed an average of 97.9% percent reduction in thrombus accumulation on the shaft surface when compared with competitive unloaded test samples.

DISCUSSION

The experimental results of the above experiments show that, other material parameters being equivalent, catheter shafts comprising a lower durometer polymer exhibited enhanced thrombo-resistance within the range of 87% to 98% relative to higher durometer venous catheter shafts, which exhibited an improved thrombus range of approximately 86%. A softer (lower) durometer base polymer exhibits a higher level of micro-hydration and/or thermal expansion than a harder (higher) durometer material when exposed to body temperatures and fluids. The increased surface area of the shaft caused by micro-swelling of the polymer compound after insertion exposes more surface area and thus more fluorine macromolecules to the blood environment. Because the fluorine deters blood components from attaching to the shaft, the softer durometer material will repel more blood components resulting in less thrombus and fibrin sheath buildup along the indwelling portion of the catheter. In addition, the softer durometer material has a greater tendency to develop surface micro-pores or "micro-cracks". These pathways through the shaft wall material may enhance the presentation of the fluorine macromolecules toward the catheter surfaces, further improving the overall effectiveness of catheter against thrombus. Thus, due to the enhanced presentation of the fluorine macromolecules caused by the material characteristics of a softer durometer polymer, the previously demonstrated thrombus reduction rates of up to 87% may be further improved to the 98% range.

DETAILS OF THE INVENTION

The present invention provides an indwelling venous access catheter comprising a shaft having a fluoropolymer additive and a polymer base. More particularly, the present invention relates to indwelling venous access catheter devices comprising a shaft having a fluoropolymer additive and a polymer base having a Shore A durometer range of less than 95. The polymer compound used to make the catheter shaft is comprised of a polymer material of a family of aliphatic, polycarbonate-based thermoplastic polyurethanes such as CARBOTHANE, a surface modifier additive comprising 1.5-2.5 percent by weight of a fluoropolymer comprising terminal polyfluor-oligomeric groups, such as ENDEXO and optionally radiopaque material sulfate comprising 25-35 percent by weight of the polymer compound, such as barium sulfate. The invention is not limited to the specific materials cited above but instead may polymer compounds in which the base polymer material is any medical grade urethane with a Shore hardness less than 95A, and an anti-thrombogenic additive. The catheter may be a PICC catheter, CVC, port catheter, dialysis catheter or other indwelling venous access device. The catheter may of any length and have various diameters and lumen configurations including single lumen, dual lumens, triple lumens. The catheter may be used acutely or for long term applications.

The present invention also provides for a method of manufacturing an indwelling venous access catheter comprising a shaft having a fluoropolymer additive and a polymer base. More particularly, the present invention relates to a method of making an indwelling venous access catheter devices comprising a shaft having a fluoropolymer additive and a polymer base having a Shore A durometer range of less than 95. The polymer compound used to make the catheter shaft is comprised of a polymer material of a family of aliphatic, polycarbonate-based thermoplastic polyurethanes such as CARBOTHANE, a surface modifier additive comprising 1.5-2.5 percent by weight of a fluoropolymer comprising terminal polyfluor-oligomeric groups, such as ENDEXO and optionally radiopaque material sulfate comprising 20-40 percent by weight of the polymer compound, such as barium sulfate. The invention is not limited to methods of making a catheter using the specific materials cited above but instead may include using a polymer compounds in which the base polymer material is any medical grade urethane with a shore hardness less than 95A, and an anti-thrombogenic or anti-infective additive. The catheter may be a PICC catheter, CVC, port catheter, dialysis catheter or other indwelling venous access device. The catheter may made to any length and have various diameters and lumen configurations including single lumen, dual lumens, triple lumens.

The present invention also provides for a method of reducing clinical complications caused by the accumulation of thrombus on the surfaces of an indwelling venous access catheter by providing a catheter shaft having a fluoropolymer additive and a polymer base of less than 95A. The polymer compound used to make the catheter shaft is comprised of a polymer material of a family of aliphatic, polycarbonate-based thermoplastic polyurethanes such as CARBOTHANE, a surface modifier additive comprising 1.5-2.5 percent by weight of a fluoropolymer comprising terminal polyfluor-oligomeric groups, such as ENDEXO and optionally radiopaque material sulfate comprising 25-35 percent by weight of the polymer compound, such as barium sulfate. The method further includes inserting the catheter of the present invention into a venous conduit wherein the catheter is comprised of a durometer less than 95A and an ENDEXO additive of 2% such that the inherent thrombo-resistance characteristics of the catheter cause an 87-98 percent reduction in the accumulation of thrombus relative to a catheter of the same composition but having a higher durometer base polymer.

The invention is not limited to the embodiments described herein. Methods of making a catheter using the specific materials cited above but instead may include using a polymer compounds in which the base polymer material is any medical grade urethane with a shore hardness less than 95A, varying the amount of radiopaque filler, the type and amount of colorant and the type of surface modifier. In addition the invention is not limited to catheter type, size or shape. and an anti-thrombogenic Various omissions, modifications, substitutions and changes in the forms and details of the device illustrated and in its operation can be made by those skilled in the art without departing in any way from the spirit of the present invention. Accordingly, the scope of the invention is not limited to the foregoing specification, but instead is given by the appended claims along with their full range of equivalents.

What is claimed is:

1. A catheter comprising:
    a catheter shaft, wherein the catheter shaft comprises:
        a polymeric material comprising polyurethane and additives, the additives comprising a fluoropolymer comprising terminal polyfluoro-oligomeric groups;
    wherein the additives comprise 1.5-2.5 percent by weight of the catheter shaft,
    wherein the fluoropolymer comprises a trimer in an amount greater than 0 and less than 5.0 percent by weight of the fluoropolymer, wherein the trimer is formed by a reaction of one equivalent of a diisocyanate with two equivalents of a perfluorinated alcohol to form a low molecular weight fluoropolymer component containing no soft segment, and
    wherein the polyurethane has a shore durometer of between 60A and 95A.

2. The catheter of claim 1, wherein the catheter shaft comprises between 25-35 percent by weight of a radiopaque material.

3. The catheter of claim 2, wherein the radiopaque material is barium sulfate.

4. The catheter of claim 1, wherein the polyurethane comprises a polycarbonate based polyurethane.

5. A method of manufacturing a catheter comprising:
    extruding a catheter shaft from a composition comprising a polyurethane and additives, the additives comprising a fluoropolymer comprising terminal polyfluoro-oligomeric groups;
    wherein the additives comprise 1.5-2.5 percent by weight of the composition,
    wherein the fluoropolymer comprises a trimer in an amount greater than 0 and less than 5.0 percent by weight of the fluoropolymer, wherein the trimer is formed by a reaction of one equivalent of a diisocyanate with two equivalents of a perfluorinated alcohol to form a low molecular weight fluoropolymer component containing no soft segment, and
    wherein the polyurethane has a shore durometer of between 60A and 95A.

6. The method of claim 5, wherein the composition comprises 25-35 percent by weight of a radiopaque material.

7. The method of claim 6, wherein the radiopaque material is barium sulfate.

8. The method of claim 5, wherein the polyurethane comprises a polycarbonate based polyurethane.

9. A method of reducing clinical complications caused by the accumulation of thrombus on the surfaces of an indwelling catheter, the method comprising:

advancing a catheter to a target site within the vasculature, the catheter comprising:
   a catheter shaft, wherein the catheter shaft comprises:
      a polymeric material comprising polyurethane and additives, the additives comprising a fluoropolymer comprising terminal polyfluoro-oligomeric groups;
   wherein the additives comprise 1.5-2.5 percent by weight of the catheter shaft,
   wherein the fluoropolymer comprises a trimer in an amount greater than 0 and less than 5.0 percent by weight of the fluoropolymer, wherein the trimer is formed by a reaction of one equivalent of a diisocyanate with two equivalents of a perfluorinated alcohol to form a low molecular weight fluoropolymer component containing no soft segment, and
   wherein the polyurethane has a shore durometer of between 60A and 95A.

10. The method of claim 9, wherein the catheter shaft comprises 25-35 percent by weight of a radiopaque material.

11. The method of claim 10, wherein the radiopaque material is barium sulfate.

12. The method of claim 9, wherein the polyurethane comprises a polycarbonate based polyurethane.

\* \* \* \* \*